(12) United States Patent
DeMattei et al.

(10) Patent No.: US 9,156,795 B2
(45) Date of Patent: *Oct. 13, 2015

(54) HYDROGEN SULFATE SALT

(75) Inventors: John DeMattei, San Diego, CA (US); Tsung-Hsun Chuang, Longmont, CO (US); Christopher John Squire, Macclesfield (GB); Ronald John Roberts, Macclesfield (GB); Gorkhn Sharma-Singh, Macclesfield (GB); Mohammed Pervez, Macclesfield (GB); James Gair Ford, Macclesfield (GB); Richard Anthony Storey, Macclesfield (GB); Paul Alfred Dickinson, Macclesfield (GB)

(73) Assignees: Array BioPharma, Inc., Boulder, CO (US); Astrazeneca AB, Sodertalje (SE)

( * ) Notice: Subject to any disclaimer, the term of this patent is extended or adjusted under 35 U.S.C. 154(b) by 516 days.

This patent is subject to a terminal disclaimer.

(21) Appl. No.: 13/463,499

(22) Filed: May 3, 2012

(65) Prior Publication Data

US 2012/0253049 A1    Oct. 4, 2012

Related U.S. Application Data

(62) Division of application No. 12/097,942, filed as application No. PCT/US2006/061895 on Dec. 12, 2006, now abandoned.

(60) Provisional application No. 60/752,781, filed on Dec. 21, 2005.

(51) Int. Cl.
C07D 235/08    (2006.01)
C07D 235/06    (2006.01)

(52) U.S. Cl.
CPC ............ *C07D 235/08* (2013.01); *C07D 235/06* (2013.01)

(58) Field of Classification Search
CPC .................................................. C07D 235/08

USPC ........................................ 548/304.4; 514/394
See application file for complete search history.

(56) References Cited

U.S. PATENT DOCUMENTS 7,235,537 B2    6/2007    Wallace et al.
7,425,637 B2    9/2008    Wallace et al.
(Continued)

FOREIGN PATENT DOCUMENTS

| WO | 03/077914 A1 | 9/2003 |
|----|--------------|--------|
| WO | 2005/023241 | 3/2005 |
| WO | 2005/023251 A1 | 3/2005 |

OTHER PUBLICATIONS

Brittain, Ed. Chapters 3 and 9 in Polymorphism in Pharmaceutical Solids, 2nd Ed.; 2009; Drugs and the pharmaceutical sciences; v. 192; Informa Healthcare; New York; pp. 52-75, 318-346.*

(Continued)

*Primary Examiner* — Timothy Thomas
(74) *Attorney, Agent, or Firm* — Fish & Richardson P.C.

(57) ABSTRACT

The present invention relates to Compound 1 hydrogen sulfate salt and solvates, crystalline forms and amorphous forms thereof, and to processes for their preparation.

Compound 1

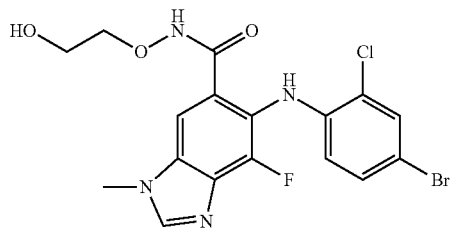

20 Claims, 3 Drawing Sheets

(56) References Cited

U.S. PATENT DOCUMENTS

| | | |
|---|---|---|
| 2003/0232869 A1 | 12/2003 | Wallace et al. |
| 2004/0116710 A1 | 6/2004 | Wallace et al. |
| 2009/0246274 A1 | 10/2009 | Bateman et al. |
| 2010/0016393 A1 | 1/2010 | DeMattei et al. |

OTHER PUBLICATIONS

US Office Action corresponding to related U.S. Appl. No. 12/411,865; dated Oct. 5, 2010, 14 pages.

International Search Report and Written Opinion corresponding to related PCT Application No. PCT/US2006/061895; dated Nov. 23, 2007, 10 pages.

Berge et al.; "Pharmaceutical Salts"; 1977; Journal of Pharmaceutical Sciences; 66(1); 1-19.

Lyssikatos et al.; ARRY-142886, a patent and selective MEK inhibitor: I) ATP-independent inhibition results in high enzymatic and cellular selective; 2004; Proc. Amer. Assoc. Cancer Res.; 45; Experimental and Molecular Therapeutics 37; Signaling Targets; Abstract #3888.

Vippagunta et al.; "Crystalline solids"; 2001 Advanced Drug Delivery Reviews; 48: 3-26.

STN "RN 606143-52-6"; entered STN 2003.

* cited by examiner

HYDROGEN SULFATE SALT

RELATED APPLICATION

The present application is a divisional application of U.S. application Ser. No. 12/097,942, filed Oct. 14, 2008, which claims priority of U.S. Provisional Application Ser. No. 60/752,781 filed Dec. 21, 2005, each of which is incorporated herein in its entirety by this reference.

BACKGROUND OF THE INVENTION

1. Field of the Invention

The present invention relates to a novel salt and, more particularly, to a novel salt of 6-(4-bromo-2-chloro-phenylamino)-7-fluoro-3-methyl-3H-benzoimidazole-5-carboxylic acid (2-hydroxy-ethoxy)-amide (hereinafter referred to as "Compound 1"), which is a MEK inhibitor that is useful in the treatment and/or prophylaxis of proliferative disease states, such as cancer, in a mammal. More specifically, the present invention relates to a hydrogen sulfate salt of Compound 1 and to processes for the preparation of said salt. Also provided are pharmaceutical compositions containing a hydrogen sulfate salt of Compound 1, and the use of the salt in the manufacture of medicaments for treatment and/or prophylaxis of proliferative disease states, such as cancer, in the human or animal body, and methods of treating proliferative disease states, such as cancer, in a mammal by administering a therapeutically effective amount of a hydrogen sulfate salt of Compound 1.

2. Description of the State of the Art

Cell signaling through growth factor receptors and protein kinases is an important regulator of cell growth, proliferation and differentiation. In normal cell growth, growth factors, through receptor activation (i.e., PDGF or EGF and others), activate MAP kinase pathways. One of the most important and most well understood MAP kinase pathways involved in normal and uncontrolled cell growth is the Ras/Raf kinase pathway. Active GTP-bound Ras results in the activation and indirect phosphorylation of Raf kinase. Raf then phosphorylates MEK1 and 2 on two serine residues (S218 and S222 for MEK1 and S222 and S226 for MEK2) (Ahn et al., *Methods in Enzymology*, 2001, 332:417-431). Activated MEK then phosphorylates its only known substrates, the MAP kinases ERK1 and 2. ERK phosphorylation by MEK occurs on Y204 and T202 for ERK1 and Y185 and T183 for ERK2 (Ahn et al., *Methods in Enzymology* 2001, 332:417-431). Phosphorylated ERK dimerizes and then translocates to the nucleus where it accumulates (Khokhlatchev et al., *Cell* 1998, 93:605-615). In the nucleus, ERK is involved in several important cellular functions, including but not limited to nuclear transport, signal transduction, DNA repair, nucleosome assembly and translocation, and mRNA processing and translation (Ahn et al., *Molecular Cell*, 2000, 6:1343-1354). Overall, treatment of cells with growth factors leads to the activation of ERK1 and 2 which results in proliferation and, in some cases, differentiation (Lewis et al., *Adv. Cancer Res.* 1998, 74: 49-139).

In proliferative diseases, genetic mutations and/or overexpression of the growth factor receptors, downstream signaling proteins, or protein kinases involved in the ERK kinase pathway lead to uncontrolled cell proliferation and, eventually, tumor formation. For example, some cancers contain mutations which result in the continuous activation of this pathway due to continuous production of growth factors. Other mutations can lead to defects in the deactivation of the activated GTP-bound Ras complex, again resulting in activation of the MAP kinase pathway. Mutated, oncogenic forms of Ras are found in 50% of colon and >90% pancreatic cancers as well as many others types of cancers (Kohl et al., *Science*, 1993, 260:1834-1837). Recently, bRaf mutations have been identified in more than 60% of malignant melanoma (Davies, H., et al., *Nature* 2002, 417:949-954). These mutations in bRaf result in a constitutively active MAP kinase cascade. Studies of primary tumor samples and cell lines have also shown constitutive or overactivation of the MAP kinase pathway in cancers of pancreas, colon, lung, ovary and kidney (Hoshino, R., et al., *Oncogene* 1999, 18:813-822). Hence, there is a strong correlation between cancers and an overactive MAP kinase pathway resulting from genetic mutations.

As constitutive or overactivation of MAP kinase cascade plays a pivotal role in cell proliferation and differentiation, inhibition of this pathway is believed to be beneficial in hyperproliferative diseases. MEK is a key player in this pathway as it is downstream of Ras and Raf. Additionally, it is an attractive therapeutic target because the only known substrates for MEK phosphorylation are the MAP kinases, ERK1 and 2. Inhibition of MEK has been shown to have potential therapeutic benefit in several studies. For example, small molecule MEK inhibitors have been shown to inhibit human tumor growth in nude mouse xenografts, (Sebolt-Leopold et al., *Nature-Medicine* 1999, 5(7):810-816; Trachet et al., AACR Apr. 6-10, 2002, Poster #5426; Tecle, H., IBC 2$^{nd}$ International Conference of Protein Kinases, Sep. 9-10, 2002), block static allodynia in animals (WO 01/05390) and inhibit growth of acute myeloid leukemia cells (Milella et al., *J. Clin. Invest.* 2001, 108 (6):851-859).

Small molecule inhibitors of MEK have been disclosed. At least thirteen patent applications have appeared in the last several years: U.S. Pat. No. 5,525,625; WO 98/43960; WO 99/01421; WO 99/01426; WO 00/41505; WO 00/42002; WO 00/42003; WO 00/41994; WO 00/42022; WO 00/42029; WO 00/68201; WO 01/68619; and WO 02/06213.

Inhibitors of the MEK are also described in WO 03/077914. 6-(4-Bromo-2-chloro-phenylamino)-7-fluoro-3-methyl-3H-benzoimidazole-5-carboxylic acid (2-hydroxy-ethoxy)-amide, or "Compound 1", is exemplified in WO 03/077914 and possesses the following structural formula:

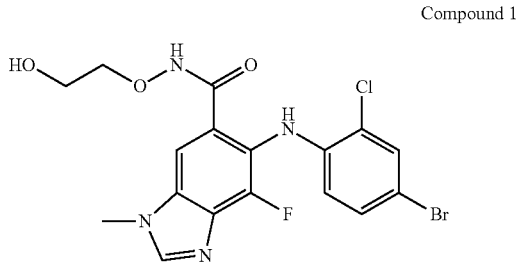 [SMILES: Cn1cnc2c(F)c(Nc3ccc(Br)cc3Cl)c(C(=O)NOCCO)cc21]

Compound 1

Compound 1 has been shown to possess inhibitory activity against MEK and therefore to be useful in the treatment of a hyperproliferative disease such as cancer.

WO 03/077914 discloses, in general terms, certain pharmaceutically acceptable salts of the compounds disclosed therein. Specifically, it is stated in WO 03/077914 that pharmaceutically acceptable salts of the compounds disclosed therein that possess a sufficiently basic moiety may form acid addition salts containing pharmaceutically acceptable anions, and a range of such anions are listed. Similarly, suitable salts of the compounds possessing an acidic moiety are to be formed by treatment of a compound with a basic compound and particularly an inorganic base.

The form of a pharmaceutically active compound which is used in medicaments is suitably one that provides for reasonable handling properties, which allow it to be processed and formulated. However, it is also necessary to ensure that the biological properties of the final formulation, such as dissolution rate of tablets and bioavailability of active ingredient are optimized, and there is frequently compromises to be made in selecting a particular form which best fulfils all these various requirements. However, in some cases, salts do not form easily and/or are not stable, which is probably due to low pKa values. The pKa value expresses the strength of acids and base, i.e., the tendency for an acid to lose a proton or a base to add a proton (Bronsted J. N., *Rec. Tray. Chim.* (1923) 47:718). This is particularly true for Compound 1.

SUMMARY OF THE INVENTION

The present invention provides a hydrogen sulfate salt (1:1 drug:$H_2SO_4$) of Compound 1 and various forms thereof, all of which are included within the scope of the invention. The salt may be in various forms, all of which are included within the scope of the invention. These forms include anhydrous forms as well as solvates. A further form may be produced by desolvating solvates. In a particular embodiment the salt is in the anhydrous form.

In a further aspect the present invention provides a method of using a hydrogen sulfate salt of Compound 1 as a medicament to treat a hyperproliferative disease or condition.

An additional aspect of the invention is the use of a hydrogen sulfate salt of Compound 1 in the preparation of a medicament for the treatment or prevention of a hyperproliferative disease or condition.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

BRIEF DESCRIPTION OF THE FIGURES

The accompanying drawings, which are incorporated herein and form a part of the specification, illustrate non-limiting embodiments of this invention, and together with the description, serve to explain the principles of the invention. In the Figures.

DETAILED DESCRIPTION

Figure 1:
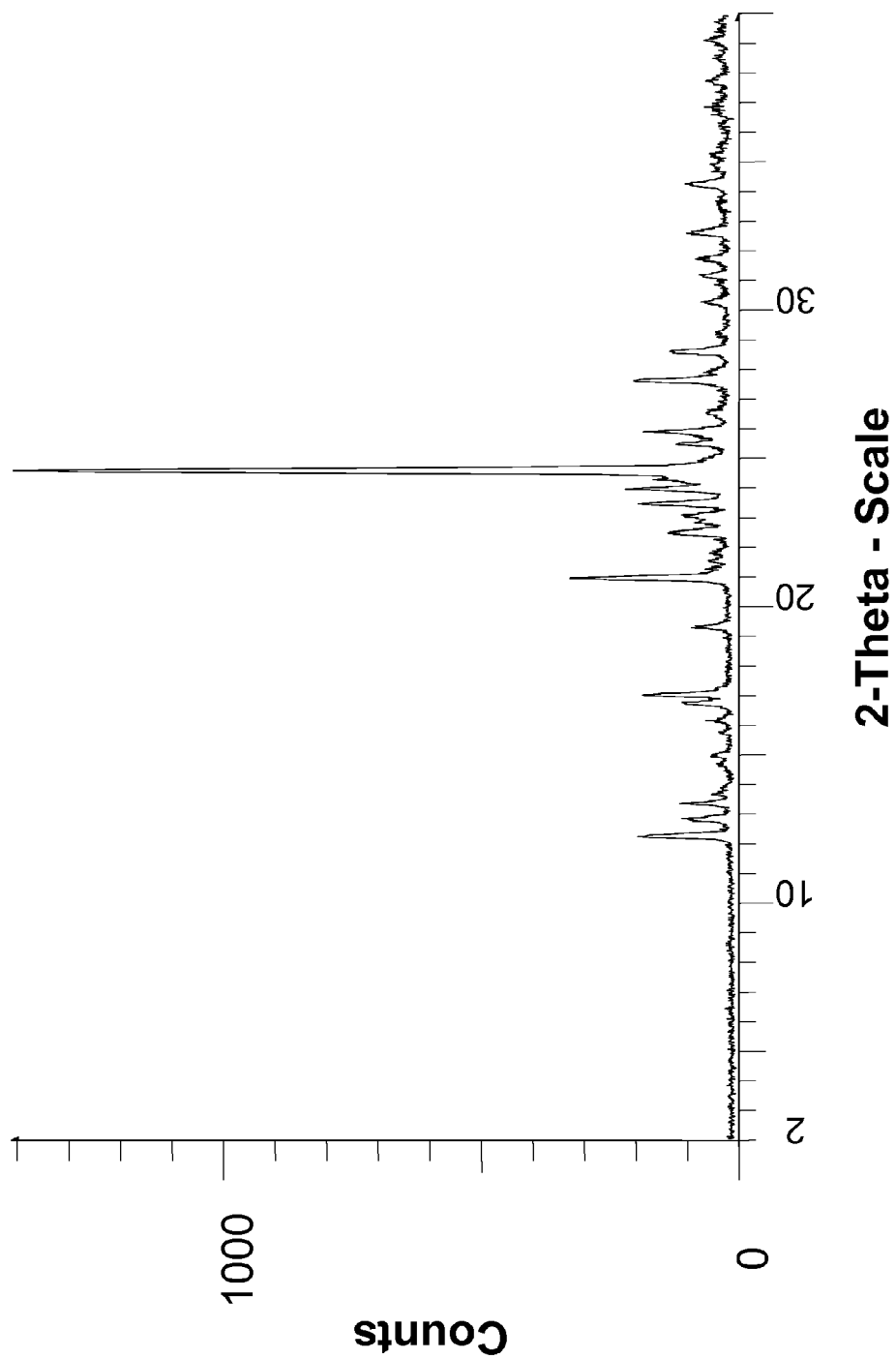
FIG. 1 shows the XRPD of the hydrogen sulfate salt of Compound 1.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

The present invention provides a hydrogen sulfate salt (1:1 drug to $H_2SO_4$) of Compound 1 and various forms thereof, all of which are included within the scope of the invention. The salt may be in various forms, all of which are included within the scope of the invention. These forms include anhydrous forms as well as solvates. A further form may be produced by desolvating solvates. In a particular embodiment, the salt is anhydrous hydrogen sulfate salt of Compound 1. Further, the present invention provides a hydrogen sulfate salt form of Compound 1 which shows unique physical and pharmaceutical properties that make it particularly suitable for use in medicaments.

In certain embodiments, salts of Compound 1 are crystalline. The crystalline salts have been found to be better than the free base in terms in their handling properties from a manufacturing point of view, in particular their static and flow properties. The formation of salts may provide a means of purification, as process impurities can be separated and salts are generally easier to isolate than the free base.

In one embodiment of the invention the hydrogen sulfate salt of Compound 1 is a crystalline salt, which has surprisingly been found to possess improved pharmaceutical properties when compared to the free base of Compound 1 and certain other salt forms of Compound 1. In particular, the dissolution rate of this crystalline salt, as well as its bioavailability has been found to be particularly high as compared to the free base and other salts, as illustrated in the examples hereinafter. The enhanced bioavailability of the hydrogen sulfate salt of Compound 1 over the free base has been shown to be independent of the formulation used for administration. The bioavailability of the free base and hydrogen sulfate forms have been compared herein when dosed in the same dispersion formulations, but similar differences in bioavailability were also observed for simple tablet formulations.

When it is stated that the present invention relates to a salt of Compound 1 which is a crystalline salt the degree of crystallinity is conveniently greater than about 60%, more conveniently greater than about 80%, preferably greater than about 90% and more preferably greater than about 95%. Most preferably the degree of crystallinity is greater than about 98%.

The extent of enhanced bioavailability offered by the hydrogen sulfate salt is surprising and is particularly useful, since the free base of Compound 1 has been classified as a BCS Class 4 compound. BCS Class 4 compounds normally have low bioavailability due to both low dissolution rate and permeability, and the limitation of permeability on absorption means that such salts would not usually be expected exert a substantial impact on absorption (See for example: Dressman et al. (2001) *Pharm Tech.* July: 68).

Suitable solvates of the hydrogen sulfate salt of Compound 1 are formed from a wide range of solvents, in particular organic solvents such as tetrahydrofuran (THF), acetonitrile (ACN), ethanol (EtOH) and methanol (MeOH). Suitable organic solvents include esters such as $C_{1-6}$ alkyl esters, for example ethyl acetate, and ketones such as $C_{1-6}$ alkyl ketones, for example methyl ethyl ketone (2-butanone).

Preparation of the salt can be effected by reacting a slurry of Compound 1 in an organic solvent and water with sulfuric acid. For preparation of a 1:1 salt approximately 1 equivalent of sulfuric acid is used. Thus in a further aspect, the invention provides a method for preparing a hydrogen sulfate salt of Compound 1, said method comprising:

(i) reacting a slurry of Compound 1 in an organic liquid and water with approximately 1 equivalent of sulfuric acid;

(ii) recovering the salt from the resultant solution; and (iii) thereafter, if desired or necessary, forming a solvate thereof.

The mole ratio of the amount of sulfuric acid to Compound 1 is suitably in the range of from 1.00:1 to 2:1, for example in a range from 1.05:1 to 1.15:1. The sulfuric acid used is suitably in the form of concentrated sulfuric acid. In a particularly embodiment, the mole ratio of sulfuric acid to Compound 1 is 1.10:1.0.

Suitably the amount of water added in step (i) is restricted to that necessary to ensure that the salt is formed. The precise amounts used will depend upon the particular nature of the solvent, the concentration of the sulfuric acid etc., but typically, the water will be present in an amount of less than 20% v/v of the total liquid present, for example from 13-17% v/v.

In a particular embodiment, the organic solvent used in step (i) is 2-butanone (methyl ethyl ketone), water is approximately 15% of the liquid volume, and the total amount of liquid used relative to Compound 1 is approximately 8 mL per gram of Compound 1.

Suitably, addition of sulfuric acid in step (i) is carried out in a controlled manner, for example at a temperature below 10° C., and the remainder of step (i) is then carried out at elevated temperature, for example from 30-90° C., as a further example in a range between 55-75° C., and as a further example at about 65° C.

Suitable organic liquids include organic solvents in which Compound 1 and its salts are sparingly soluble. As used herein, the expression "sparingly soluble" means having a solubility less than 100 mL of solvent per gram of solute, for example between 30 and 100 mL of solvent per gram of solute. These solvents include alkyl ketones, for example $C_{1-6}$ alkyl ketones such as 2-butanone, alcohols such as $C_{1-6}$ alcohols, for example methanol or ethanol, and esters such as $C_{1-6}$ alkyl esters, for example as ethyl acetate. In one embodiment, the organic solvent is methyl ethyl ketone (2-butanone).

Suitably, the reaction mixture is filtered between steps (i) and (ii) to remove any extraneous material. The residue is optionally washed, for example with a mixture of the organic liquid and water, and the desired salt crystallized from the filtrate, which may optionally be combined with the wash solution.

In certain embodiments, the hydrogen sulfate salt is recovered in step (ii) by cooling the reaction mixture, optionally with the addition of further organic liquid, so that the hydrogen sulfate salt is precipitated. The further organic liquid may be the same organic liquid as used in step (i), or it may be a different organic liquid, provided this acts as an anti-solvent for the hydrogen sulfate salt of Compound 1. Seeding of the solution with crystals of the hydrogen sulfate salt of Compound 1 may assist in the precipitation process.

In one embodiment, prior to cooling, the filtrate is first subjected to a distillation step to remove water and to ensure that the salt is recovered in an acceptable yield. In a particular embodiment the solvent is 2-butanone and the filtrate is distilled at atmospheric pressure.

On cooling, the salt can be recovered from the resultant slurry for example by filtration. The recovered material may then be dried for example at elevated temperature, for example of from 40-60° C., and as another example at about 50° C., until constant weight is achieved. If the product is a solvate with the organic liquid such as methanol, it may be de-solvated if desired at this time by heating.

The physical properties of the hydrogen sulfate salt were investigated and are described further in the Examples.

The invention also includes isotopically-labeled compounds, which are identical to those recited in the present invention, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. The hydrogen sulfate salt of Compound 1 and polymorphs thereof which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$ and carbon-14, i.e., $^{14}C$, isotopes are particularly widely used as a result of their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be utilized in some particular circumstances. Isotopically labeled salts of the present invention can generally be prepared by carrying out procedures disclosed in WO 03/077914 by substituting a readily available isotopically labeled reagent for a non-isotopically labeled reagent during the preparation, or if desired, using an isotopically labeled sulfuric acid in the preparation of the salt.

The composition may be in a form suitable for oral administration (for example as tablets, lozenges, hard or soft capsules, emulsions, dispersible powders or granules, syrups, elixirs or oily or extemporaneously prepared aqueous suspensions), for administration by inhalation (for example as a finely divided powder or a liquid aerosol), for administration by insufflation (for example as a finely divided powder), for parenteral injection (for example as a sterile solution, suspension or emulsion for intravenous, subcutaneous, intramuscular, intravascular or infusion dosing), for topical administration (for example as creams, ointments, gels, oily solutions or suspensions or extemporaneously prepared aqueous suspensions), or for rectal administration (for example as a suppository). In one embodiment, the hydrogen sulfate salt of Compound 1 is administered orally. In general the above compositions may be prepared in a conventional manner using conventional excipients.

The amount of the active compound administered will be dependent on the subject being treated, the severity of the disorder or condition, the rate of administration, the disposition of the compound and the discretion of the prescribing physician. However, an effective dosage is in the range of about 0.01 to about 100 mg per kg body weight per day, preferably about 1 to about 35 mg/kg/day, in single or divided doses. For a 70 kg human, this would amount to about 0.7 to 7000 mg/day, preferably about 70 to about 2500 mg/day. In some instances, dosage levels below the lower limit of the aforesaid range may be more than adequate, while in other cases still larger doses may be employed without causing any harmful side effect, provided that such larger doses are first divided into several small doses for administration throughout the day. A unit dosage form such as a tablet or capsule will usually contain, for example 1-1000 mg of active ingredient, and preferably 5-420 mg of active ingredient. Preferably a daily dose in the range of 0.03-6 mg/kg is employed.

According to a further aspect of the present invention there is provided a hydrogen sulfate salt of Compound 1 as defined herein for use in a method of treatment or prophylaxis of the human or animal body by therapy. A further feature of the present invention is hydrogen sulfate salt of Compound 1 as defined herein for use as a medicament. In a further aspect, the present invention provides hydrogen sulfate salt of Compound as defined herein for use as a medicament for the treatment of disease states mediated through MEK, in particular proliferative disorders, or abnormal cell growth, such as cancer, in a warm-blooded mammal such as a human. Accordingly, a further aspect of the invention provides the use of hydrogen sulfate salt of Compound 1 as defined herein in the manufacture of a medicament for use in the treatment of disease states mediated through the MEK, in particular proliferative disorders, or abnormal cell growth, such as cancer, in a warm-blooded mammal such as a human.

According to a further feature of the invention there is provided a method for treating disease states mediated through the MEK, in particular proliferative disorders, or abnormal cell growth, such as cancer, in a warm-blooded mammal, such as a human, in need of such treatment which comprises administering to said mammal an effective amount of an hydrogen sulfate salt of Compound 1 hydrogen sulfate salt as herein, or a pharmaceutical composition as defined herein.

Particular examples of proliferative disorders, which may be treated using the salts or compositions of the invention, include hyperproliferative disorders in a mammal Particular cancers are brain, lung, squamous cell, bladder, gastric, pancreatic, breast, head, neck, renal, kidney, ovarian, prostate, colorectal, esophageal, testicular, gynecological or thyroid cancer.

However, the compounds and compositions of the invention may also be used in the treatment of a non-cancerous hyperproliferative disorder such as benign hyperplasia of the skin (e.g., psoriasis), restenosis, or prostate (e.g., benign prostatic hypertrophy (BPH)).

Other examples of MEK mediated diseases, which may be treated using the compounds, or compositions of the invention include pancreatitis or kidney disease (including proliferative glomerulonephritis and diabetes-induced renal disease) or the treatment of pain in a mammal.

The compounds and compositions may also be used for the prevention of blastocyte implantation in a mammal, or for treating a disease related to vasculogenesis or angiogenesis in a mammal. Such diseases may include tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The terms "abnormal cell growth" and "hyperproliferative disorder" are used interchangeably in this application and refer to cell growth that is independent of normal regulatory mechanisms (e.g., loss of contact inhibition). This includes, for example, the abnormal growth of: (1) tumor cells (tumors) that proliferate by expressing a mutated tyrosine kinase or over expression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The term "treating", as used herein, unless otherwise indicated, means reversing, alleviating, inhibiting the progress of, or preventing the disorder or condition to which such term applies, or one or more symptoms of such disorder or condition. The term "treatment" as used herein, unless otherwise indicated, refers to the act of treating as "treating" is defined immediately above.

Thus patients that can be treated with compounds or compositions of the present invention include, for example, patients that have been diagnosed as having psoriasis, restenosis, atherosclerosis, BPH, lung cancer, non small cell lung cancer, bone cancer, CMML, pancreatic cancer, colorectal, skin cancer, cancer of the head and neck, melanoma (in particular cutaneous or intraocular melanoma), uterine cancer, ovarian cancer, rectal cancer, cancer of the anal region, stomach cancer, colon cancer, breast cancer, testicular, gynecologic tumors (e.g., uterine sarcomas, carcinoma of the fallopian tubes, carcinoma of the endometrium, carcinoma of the cervix, carcinoma of the vagina or carcinoma of the vulva), ovarian cancer, multiple myeloma, hepatocellular carcinoma, Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, in particular acute myeloid leukaemia solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

The hydrogen sulfate salt of Compound 1 may be applied as a sole therapy or may involve, in addition to the hydrogen sulfate salt of Compound 1, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to Compound 1 hydrogen sulfate salt may be surgery, radiotherapy or chemotherapy. Such chemotherapy may cover categories of therapeutic agent such as:

(i) antiangiogenic agents such as those which inhibit the effects of vascular endothelial growth factor, (for example the anti-vascular endothelial cell growth factor antibody bevacizumab [Avastin™], and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856 and WO 98/13354 and those that work by different mechanisms from those defined herein (for example linomide, inhibitors of integrin αvβ3 function, angiostatin, razoxin, thalidomide, MMP-2 (matrix-metalloprotienase 2)

inhibitors, MMP-9 (matrix-metalloprotienase 9) inhibitors, and COX-II (cyclooxygenase II) inhibitors), and (ii) vascular targeting agents (for example combretastatin phosphate and compounds disclosed in WO 00/40529, WO 00/41669, WO 01/92224, WO 02/04434 and WO 02/08213, and the vascular damaging agents described in International Patent Application Publication No. WO 99/02166, (for example N-acetylcolchinol-O-phosphate));

(iii) cytostatic agents such as antioestrogens (for example tamoxifen, toremifene, raloxifene, droloxifene, and iodoxyfene), oestrogen receptor down regulators (for example fulvestrant), progestogens (for example megestrol acetate), aromatase inhibitors (for example anastrozole, letrazole, vorazole, and exemestane), antiprogestogens, antiandrogens (for example flutamide, nilutamide, bicalutamide, and cyproterone acetate), LHRH agonists and antagonists (for example goserelin acetate, leuprorelin, and buserelin), inhibitors of 5α-reductase (for example finasteride);

(iv) anti-invasion agents (for example metalloproteinase inhibitors like marimastat and inhibitors of urokinase plasminogen activator receptor function or antibodies to Heparanese;

(v) inhibitors of growth factor function (such growth factors include for example platelet derived growth factor and hepatocyte growth factor), such inhibitors include growth factor antibodies, growth factor receptor antibodies, (for example the anti-erbb2 antibody trastuzumab [Herceptin™], the anti-EGFR antibody panitumumab, the anti-erbB1 antibody cetuximab [C225]), and any growth factor or growth factor receptor antibodies disclosed by Stern et al. Critical reviews in oncology/haematology, 2005, Vol. 54, pp 11-29); such inhibitors also include tyrosine kinase inhibitors such as inhibitors of the epidermal growth factor family (for example EGFR family tyrosine kinase inhibitors such as N-(3-chloro-4-fluorophenyl)-7-methoxy-6-(3-morpholinopropoxy)-quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)) and erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(vi) antiproliferative/antineoplastic drugs and combinations thereof, as used in medical oncology, such as antimetabolites (for example antifolates such as methotrexate, fluoropyrimidines such as 5-fluorouracil, tegafur, purine and adenosine analogues, and cytosine arabinoside, hydroxyurea or, for example, one of the anti-metabolites specifically disclosed in European Patent Application No. 239362 such as N-(5-[N-(3,4-dihydro-2-methyl-4-oxoquinazolin-6-ylmethyl)-N-methylamino-2-thenoyl)-L-glutamic acid; antitumour antibiotics (for example anthracyclines such as adriamycin, bleomycin, doxorubicin, daunomycin, epirubicin and idarubicin, mitomycin-C, dactinomycin, and mithramycin); platinum derivatives (for example cisplatin, and carboplatin); alkylating agents (for example nitrogen mustard, melphalan, chlorambucil, busulphan, cyclophosphamide, ifosfamide, nitrosoureas, and thiotepa); antimitotic agents (for example vinca alkaloids such as vincristine, vinblastine, vindesine, and vinorelbine, and taxoids such as taxol and taxotere); topoisomerase inhibitors (for example epipodophyllotoxins such as etoposide and teniposide, amsacrine, topotecan, camptothecin and irinotecan); enzymes (for example asparaginase); and thymidylate synthase inhibitors (for example raltitrexed);

and additional types of chemotherapeutic agent including:

(vii) biological response modifiers (for example interferon);

(viii) antibodies (for example edrecolomab);

(ix) antisense therapies, for example those which are directed to the targets listed above, such as ISIS 2503, an anti-ras antisense;

(x) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (xi) immunotherapy approaches, including for example ex-vivo and in vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

For example, a hydrogen sulfate salt of Compound 1 may be used in conjunction with an effective amount of one or more substances selected from anti-angiogenesis agents, signal transduction inhibitors, and antiproliferative agents.

In a particular embodiment, anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a Compound 1 hydrogen sulfate salt of the present invention and pharmaceutical compositions described herein. Examples of useful COX-II inhibitors include CELEBREX™ (alecoxib), valdecoxib, and rofecoxib. Examples of useful matrix metalloprotienase inhibitors are described in WO 96/33172, WO 96/27583, WO 98/07697, WO 98/03516, WO 98/34918, WO 98/34915, WO 98/33768, WO 98/30566, WO 90/05719, WO 99/52910, WO 99/52889, WO 99/29667, U.S. Pat. No. 5,863,949, and U.S. Pat. No. 5,861,510, all of which are incorporated herein in their entireties by reference. Suitable MMP-2 and MMP-9 inhibitors are those that have little or no activity inhibiting MMP-1. In particular, those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13) are used. Particular examples of MMP inhibitors useful in the present invention are AG-3340, RO 32-3555, and RS 13-0830.

Therefore, a further aspect of the present invention the hydrogen sulphate salt of Compound 1 in combination with any one of the anti tumour agents listed under (i)-(xi) herein above. A further aspect of the present invention provides the hydrogen sulphate salt of Compound 1 in combination with one or more of the anti tumour agents listed under (i)-(xi) herein above. A further aspect of the present invention provides the hydrogen sulphate salt of Compound 1 in combination with any one of the classes of anti-tumour agents listed under (i)-(xi) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the present invention there is provided a kit comprising the hydrogen sulphate salt of Compound 1 in combination with an anti-tumour agent selected from one listed under (i)-(xi) herein above.

According to a further aspect of the present invention there is provided a kit comprising:

a) the hydrogen sulphate salt of Compound 1 in a first unit dosage form;

b) an anti-tumour agent selected from one listed under (i)-(xi) herein above; in a second unit dosage form; and c) container means for containing said first and second dosage forms.

Compound 1 has been found to have activity in the following assay. N-terminal 6 His-tagged, constitutively active MEK1 (2-393) is expressed in *E. coli* and protein is purified by conventional methods (Ahn et al., *Science* 1994, 265:966-970). The activity of MEK1 is assessed by measuring the incorporation of γ-$^{33}$P-phosphate from γ-$^{33}$P-ATP onto N-terminal His tagged ERK2, which is expressed in *E. coli* and is purified by conventional methods, in the presence of MEK1. The assay is carried out in 96-well polypropylene plate. The incubation mixture (100 μL) comprises of 25 mM Hepes, pH 7.4, 10 mM MgCl$_2$, 5 mM β-glycerolphosphate, 100 μM sodium orthovanadate, 5 mM DTT, 5 nM MEK1, and 1 μM ERK2. Inhibitors are suspended in DMSO, and all reactions, including controls are performed at a final concentration of 1% DMSO. Reactions are initiated by the addition of 10 μM ATP (with 0.5 μCi γ-$^{33}$P-ATP/well) and incubated at ambient temperature for 45 minutes. Equal volume of 25% TCA is added to stop the reaction and precipitate the proteins. Precipitated proteins are trapped onto glass fiber B filterplates, and excess labeled ATP washed off using a Tomtec MACH III harvestor. Plates are allowed to air-dry prior to adding 30 μL/well of Packard Microscint 20, and plates are counted using a Packard TopCount. In this assay, Compound 1 exhibited an IC$_{50}$ of less than 50 micromolar.

EXAMPLES

In order to illustrate the invention, the following examples are included. However, it is to be understood that these examples do not limit the invention and are only meant to suggest a method of practicing the invention. Yields are given for the Examples as performed and could likely be enhanced through further development. The $^1$H NMR spectrum (400 MHz) was referenced to TMS (0.00 ppm), $^{13}$C NMR spectrum (100 MHz) was referenced to the NMR solvent (39.5 ppm) and the $^{19}$F NMR spectrum was referenced to trichlorofluoromethane (0.00 ppm). FTIR spectra were obtained on a Nicolet Magna 860 ESP FTIR Spectrometer in various ways including from a 2% w/w dispersion of this material in powdered KBr, using the DRIFTS sampling technique, over the 4,000-400 cm$^{-1}$ mid-infrared spectral region.

Example 1

Preparation of the Hydrogen Sulfate Salt of Compound 1

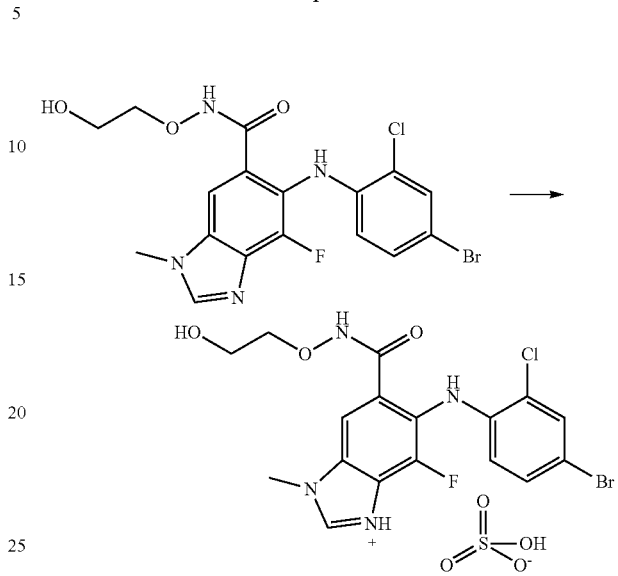

To a stirred suspension of 6-(4-bromo-2-chloro-phenylamino)-7-fluoro-3-methyl-3H-benzoimidazole-5-carboxylic acid (2-hydroxy-ethoxy)-amide (100 g, 0.206 mol) (obtainable as described in Example 10 of WO 03/077914, which is incorporated herein by reference and as described below) in 2-butanone (680 mL) and water (115 mL) at 0-5° C. was added sulfuric acid (12.3 mL, 0.226 mol) followed by water (5 mL) maintaining a temperature of 10° C. or lower. The stirred mixture was heated to 65° C. and held for 30 minutes before filtering to remove any extraneous matter. The filter was washed with a mixture of 2-butanone (85 mL) and water (15 mL). The combined filtrates were heated to 72° C. before adding 2-butanone (500 mL) maintaining a temperature of between 60-72° C. The resulting mixture was distilled at atmospheric pressure (approximate distillation temperature 73-74° C.) until 500 mL of distillate had been collected.

A second aliquot of 2-butanone (500 mL) was added, maintaining the temperature of the mixture above 70° C. The resulting mixture was distilled again until 250 mL of distillate had collected. The mixture was cooled to 0-5° C. over approximately 1 hour. The resulting slurry was filtered, washed with 2-butanone (240 mL) and dried under reduced pressure at 50° C., until a constant weight was achieved, to give 6-(4-bromo-2-chloro-phenylamino)-7-fluoro-3-methyl-3H-benzoimidazole-5-carboxylic acid (2-hydroxy-ethoxy)-amide hydrogen sulfate (103.5 g, 0.186 mol, 90% yield) as an off white crystalline solid. $^1$H NMR (400 MHz, D$_6$ DMSO) δ 3.58 (2H, t, CH$_2$OH), 3.89 (2H, t, CH$_2$ON), 3.99 (3H, s, CH$_3$), 6.47 (1H, dd, ArH), 7.29 (1H, dd, ArH), 7.63 (1H, d, ArH), 7.91 (1H, s, ArH), 7.96 (3H, br, ROH, NH, SOH), 8.10 (1H, br, ArNH), 8.94 (1H, s, NCHN), 11.79 (1H, s, ONH). $^{13}$C NMR (100 MHz, D$_6$ DMSO) δ 32.1 (CH$_3$), 58.5 (CH$_2$OH), 77.3 (CH$_2$ON), 108.2 (CH), 109.6 (CBr), 115.8 (CH), 120.6 (CCl), 122.0 (C), 125.0 (CC=O), 129.4 (C), 130.5 (CH), 131.1 (CH), 132.3 (C), 140.6 (C), 145.8 (CF), 146.5 (CH), 164.2 (C=O).

Figure 2:
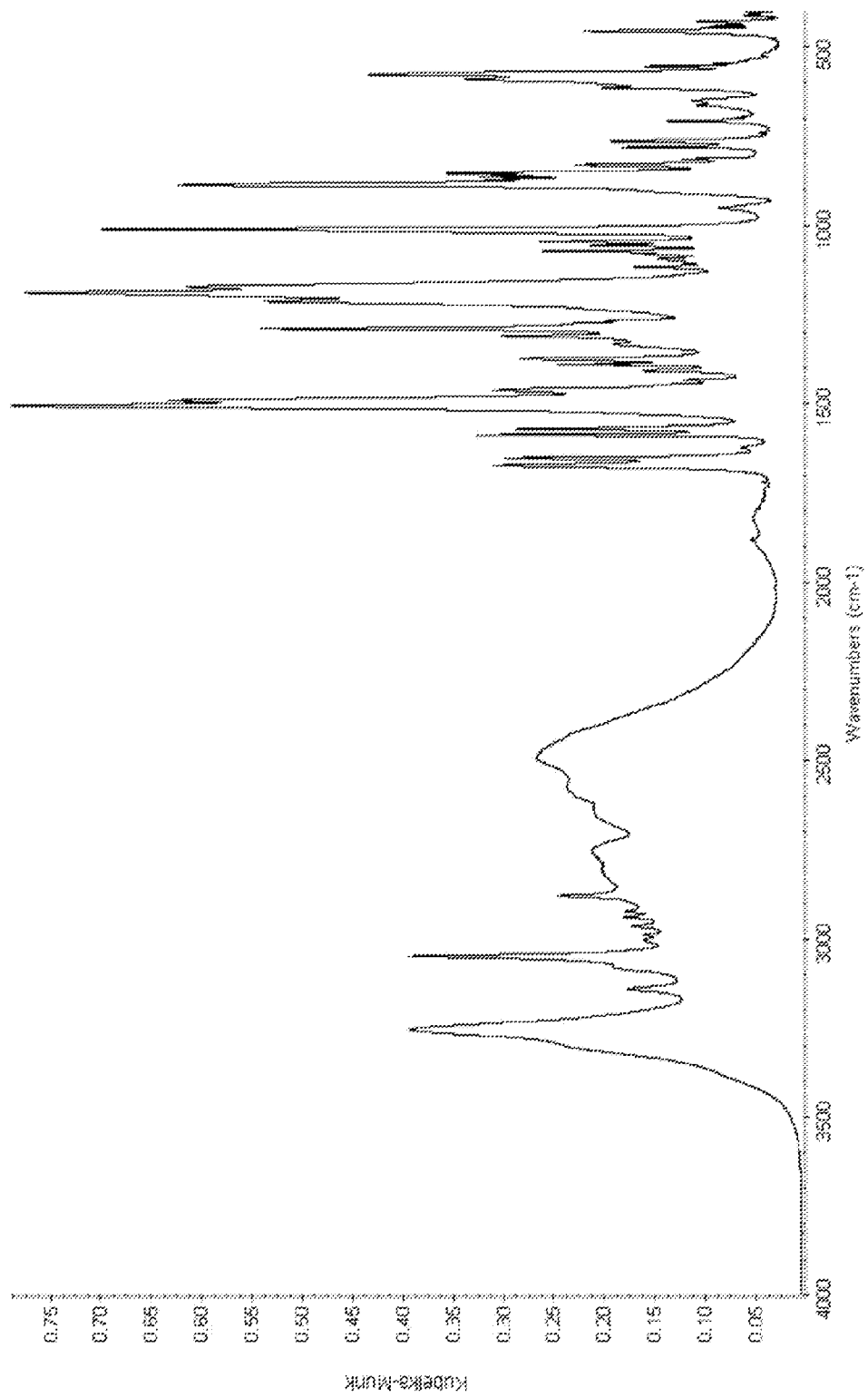
FIG. 2 shows the infrared spectrum of the hydrogen sulfate salt of Compound 1 obtained using the DRIFTS sampling technique.

The results of the infrared analysis are shown in FIG. 2. Spectral assignments are summarized in Table 1.

TABLE 1

| Wavenumber (cm$^{-1}$) | Assignment |
|---|---|
| 3,255 | Includes the O—H stretching vibration of the primary alcohol group and the N—H stretching vibrations of the secondary aromatic amine and secondary amide groups. |
| 3,200-2,700 | Includes =C—H stretching vibrations of the aromatic ring and benzimidazole group and the aliphatic C—H stretching vibrations. |
| 2,700-2,300 | Includes the multiple NH$^+$ stretching vibrations of the benzimidazole 1:1 sulfate salt group. |
| 1,673 | C=O stretching vibrations of the secondary amide |
| 1,653 | group where the carbonyl group is subject to different environmental effects such as hydrogen bonding. |
| 1,640-1,370 | Includes the C=C aromatic ring stretching vibrations, the C=C and C=N stretching vibrations of the benzimidazole group, the O—H deformation vibration of the primary alcohol group and the aliphatic C—H deformation vibrations. |
| 1,570 | The CNH combination band of the secondary amide group. |
| 1,506 | Includes the CNH bending vibration of the secondary aromatic amine group. |
| 1,213 | The aryl C—F stretching vibration. |
| 1,189 | The asymmetric SO$_3^-$ stretching vibration of the benzimidazole 1:1 sulfate salt group. |
| 1,100-1,000 | Includes the C—O stretching vibration of the primary alcohol group and the aryl C—Br stretching vibration. |
| 1,011 | The symmetric SO$_3^-$ stretching vibration of the benzimidazole 1:1 sulfate salt group. |
| 920-600 | Includes the C—H wag vibrations and C=C ring bending vibrations of the 1,2,4-trisubtituted aromatic ring and the benzimidazole group. |
| 888 | Includes the S—O(H) stretching vibration of the benzimidazole 1:1 sulfate salt group. |

Example 1A

Preparation of the Hydrogen Sulphate Salt of Compound 1

Sulfuric acid (1.52 ml, 27.86 mmol) was added to a stirred suspension of 6-(4-bromo-2-chlorophenylamino)-7-fluoro-3-methyl-3H-benzoimidazole-5-carboxylic acid (2-hydroxy-ethoxy)-amide (10 g, 0.0214 mol) (obtainable as described in Example 10 of WO 03/077914, which is incorporated herein by reference and as described below) in tetrahydrofuran (THF) (62 ml) and water (8 ml) whilst maintaining a temperature of 10° C. or lower. The stirred mixture was heated to 65° C. and held for 30 minutes before filtering to remove any extraneous matter. THF (150 ml) was then added to the mixture maintaining the temperature above 60° C. The mixture was then cooled to 0-5° C. over approximately 2 hour. The resulting slurry was filtered, washed with THF (30 ml) and dried under reduced pressure at 50° C. until a constant weight was achieved, to give 6-(4-bromo-2-chlorophenylamino)-7-fluoro-3-methyl-3H-benzoimidazole-5-carboxylic acid (2-hydroxyethoxy)-amide hydrogen sulfate (9.81 g, 0.17 mol, 82% yield) as an off white crystalline solid. The material was the same as that produced in Example 1 above.

Example 1B

Preparation of 6-(4-bromo-2-chloro-phenylamino)-7-fluoro-3-methyl-3H-benzoimidazole-5-carboxylic acid (2-hydroxy-ethoxy)-amide Step A: 2,3,4-Trifluoro-5-nitro-benzoic acid A 3 liter three neck round bottom flask was charged with 125 ml H$_2$SO$_4$. Fuming nitric acid was added (8.4 ml, 199 mmol) and the mixture gently stirred. 2,3,4-Trifluorobenzoic acid (25 g, 142 mmol) was added in 5 g portions over 90 minutes. The dark brownish yellow solution was stirred for 60 minutes at which time the reaction was complete. The reaction mixture was poured into 1 liter of an ice:water mixture and extracted with diethyl ether (3×600 ml). The combined extracts were dried (MgSO$_4$) and concentrated under reduced pressure to give a yellow solid. The solid was suspended in hexanes and stirred for 30 min after which time it was filtered to give 29 g (92%) of clean desired product as an off-yellow solid: MS APCI (−) m/z 220 (M−1) detected.

Step B: 4-Amino-2,3-difluoro-5-nitro-benzoic acid

Ammonium hydroxide solution (~30% in water) (35 ml, 271 mmol) was added to a solution of 2,3,4-trifluoro-5-nitrobenzoic acid (15 g, 67.8 mmol) in 30 ml water at 0° C. with stirring. Upon completion of the ammonium hydroxide addition, the reaction mixture was warmed to room temperature with stirring. After 2.5 hours, the reaction mixture was cooled to 0° C. and concentrated HCl was carefully added until pH of reaction mixture was 0. The reaction mixture was diluted with water (30 ml) and extracted with diethyl ether (3×50 ml). The combined organic extracts were dried (MgSO$_4$) and concentrated under reduced pressure to give 14 g (95%) of pure desired product: MS APCI (−) m/z 217 (M−1) detected.

Step C: 4-amino-2,3-difluoro-5-nitrobenzoic acid methyl ester

A 2 M solution of tetramethylsilane (TMS) diazomethane in hexanes (6.88 ml, 13.75 mmol) was added to a suspension of 4-amino-2,3-difluoro-5-nitrobenzoic acid (2.00 g, 9.17 mmol) in 25 ml of 4:1 Tetrahydrofuran (THF):MeOH at 0° C. under nitrogen atmosphere. Upon completion of addition, reaction mixture was warmed to room temperature. After 0.5 hours, excess TMS diazomethane was destroyed by the careful addition of acetic acid. The reaction was then concentrated under reduced pressure and dried in vacuo 1.95 g (92%) of pure desired product: MS APCI (−) m/z 231 (M−1) detected.

Step D: 4-Amino-3-fluoro-5-nitro-2-phenylamino-benzoic acid methyl ester

4-Amino-2,3-difluoro-5-nitrobenzoic acid methyl ester (23.48 g, 101.1 mmol) was suspended in xylenes (125 ml) and aniline (92 ml, 1011 mmol) was added. The reaction mixture was stirred at 125° C. for 16 hours under N$_2$. The reaction mixture was cooled to room temperature and solids precipitated out of solution. The solids were collected by filtration and washed with xylenes and then diethyl ether. Recovered 22.22 g (72.78 mmol) of yellow solid which was pure desired product. The filtrate was concentrated under reduced pressure, redissolved in methylene chloride and flushed through a plug of silica gel eluting with methylene chloride. The desired fractions were concentrated under reduced pressure to give a brown solid which was triturated with diethyl ether to give 5.47 g (17.91 mmol) of yellow solid which was pure desired product. Combined product yield was 27.69 g (90%). MS APCI (−) m/z 304 (M−1) detected.

Step E: 7-Fluoro-6-phenylamino-3H-benzoimidazole-5-carboxylic acid methyl ester

4-Amino-3-fluoro-5-nitro-2-phenylamino-benzoic acid methyl ester (16.70 g, 54.71 mmol), formic acid (250 ml, 6.63 mol) and 20% Pd(OH)$_2$/C (9.00 g, 16.91 mmol) in ethanol (250 mL) were stirred at 40° C. for two hours under N$_2$ and then at 95° C. for 16 hours. The reaction mixture was cooled to room temperature and filtered through Celite rinsing with ethyl acetate. The filtrate was concentrated under reduced pressure to give a yellow solid. The solid was triturated with diethyl ether to give 13.47 g (86%) of the desired product as a tan solid. MS APCI (+) M/Z 286 (M+1) detected; MS APCI (−) m/z 284 (M−1) detected.

Step F: 6-(4-Bromo-phenylamino)-7-fluoro-3H-benzoimidazole-5-carboxylic acid methyl ester 7-Fluoro-6-phenylamino-3H-benzoimidazole-5-carboxylic acid methyl ester (4.99 g, 17.51 mmol) was dissolved in N,N-dimethylformamide (275 ml). N-bromosuccinimide (3.15 g, 17.70 mmol) was added as a solid and the reaction mixture was stirred at room temperature under N$_2$. After 30 minutes, the reaction mixture was quenched by the addition of aqueous saturated sodium bisulfite solution. The reaction mixture was then poured into a separatory funnel, diluted with water and ethyl acetate and the layers separated. The aqueous layer was extracted with ethyl acetate. The combined organic extracts were washed three times with water, once with brine and then dried (Na$_2$SO$_4$) and concentrated under reduced pressure to yield 6.38 g (100%) of the pure desired product as a tan solid. MS ESI (+) m/z 364, 366 (M+Br pattern) detected.

Step G: 6-(4-Bromo-2-chloro-phenylamino)-7-fluoro-3H-benzoimidazole-5-carboxylic acid methyl ester 6-(4-Bromo-phenylamino)-7-fluoro-3H-benzoimidazole-5-carboxylic acid methyl ester (6.38 g, 17.51 mmol), was dissolved in N,N-dimethylformamide (275 mL). N-chlorosuccinimide (2.36 g, 17.70 mmol) was added as a solid and the reaction mixture was stirred at room temperature under N$_2$ until the reaction is complete (5-6 days). The reaction mixture was quenched by the addition of aqueous saturated sodium bisulfite solution to give a suspension. The resulting solids were collected by filtration, washed with water and diethyl ether and dried under reduced pressure to yield 6.07 g (87%) of the pure desired product as a beige solid. MS ESI (+) m/z 398, 400 (M+Br pattern) detected.

Step H: 6-(4-Bromo-2-chlorophenylamino)-7-fluoro-3-methyl-3H-benzoimidazole-5-carboxylic acid methyl ester and 6-(4-Bromo-2-chlorophenylamino)-7-fluoro-1-methyl-1H-benzoimidazole-5-carboxylic acid methyl ester A solution of 6-(4-bromo-2-chloro-phenylamino)-7-fluoro-3H-benzoimidazole-5-carboxylic acid methyl ester (150 mg, 0.38 mmol), iodomethane (28 µL, 0.45 mmol) and potassium carbonate (78 mg, 0.56 mmol) in dimethylformamide (1.5 mL) was stirred at 75° C. for one hour. The reaction mixture was diluted with ethyl acetate, washed with saturated aqueous potassium carbonate (2×), brine and dried (Na$_2$SO$_4$). Flash column chromatography (20:1 methylene chloride/ethyl acetate) provided 56 mg (36%) of the more mobile 6-(4-bromo-2-chlorophenylamino)-7-fluoro-3-methyl-3H-benzoimidazole-5-carboxylic acid methyl ester as a white solid. $^{19}$F NMR (376 MHz, CD$_3$OD)—133.5 (s). MS APCI (+) m/z 412, 414 (M+, Br pattern) detected. Also isolated is 54 mg (35%) of 6-4(-bromo-2-chloro-phenylamino)-7-fluoro-1-methyl-1H-benzoimidazole-5-carboxylic acid methyl ester as a white solid. $^{19}$F NMR (376 MHz, CD$_3$OD)—139.9 (s). MS APCI (+) m/z 412, 414 (M+, Br pattern) detected.

Step I: 6-(4-Bromo-2-chloro-phenylamino)-7-fluoro-3-methyl-3H-benzoimidazole-5-carboxylic acid 6-(4-Bromo-2-chloro-phenylamino)-7-fluoro-3-methyl-3H-benzoimidazole-5-carboxylic acid methyl ester (56 mg, 0.14 mmol) was dissolved into 2:1 THF/water (3 mL) and NaOH (0.55 ml, 1.0 M aqueous solution, 0.55 mmol) was added. After stirring for two hours the reaction was reduced to one quarter initial volume via rotary evaporation and the remainder diluted to 50 ml with water. The aqueous solution was acidified to pH 2 by the addition of 1.0 M aqueous HCl and extracted with 1:1 tetrahydrofuran/ethyl acetate (3×), dried (Na$_2$SO$_4$) and concentrated under reduced pressure to provide 43 mg (79%) pure carboxylic acid as an off white solid. MS ESI (+) m/z 397, 398 (M+, Br pattern) detected.

Step J: 6-(4-Bromo-2 chloro-phenylamino-7-fluoro-3-methyl-3H-benzoimidazole-5-carboxylic acid (2-vinyloxy-ethoxy)-amide 6-(4-Bromo-2-chloro-phenylamino)-7-fluoro-3-methyl-3H-benzoimidazole-5-carboxylic acid (2.00 g, 5.0 mmol), O-(2-vinloxy-ethyl)-hydroxylamine (0.776 g, 7.5 mmol), HOBt (0.88 g, 6.5 mmol), triethylamine (1.61 mL, 2.3 mmol) and EDCl (1.3 g, 6.5 mmol) were dissolved in dimethylformamide (52 mL), and stirred at room temperature for 48 hours. The reaction mixture was diluted with ethyl acetate, washed with water (3×), saturated potassium carbonate (2×), saturated ammonium chloride (2×), brine, dried (Na$_2$SO$_4$) and concentrated under reduced pressure to an off-white solid. Trituration of the solid with diethyl ether provided 2.18 g (90%) desired product as an off-white solid. MS ESI (=) m/z 483, 485 (M+Br pattern) detected.

Step K: 6-(4-Bromo-2-chloro-phenylamino)-7-fluoro-3-methyl-3H-benzoimidazole-5-carboyxlic acid (2-hydroxy-ethoxy)-amide Hydrochloric acid (14 mL, 1.0 M aqueous solution, 14 mmol) was added to a suspension of 6-(4-bromo-2-chloro-phenylamino)-7-fluoro-3-methyl-3H-benzoimidazole-5-carboyxlic acid (2-vinyloxyethoxy)-amide (2.18 g, 4.50 mmol) in ethanol (50 mL) and the reaction mixture allowed to stir for 24 hours. The reaction mixture was concentrated to dryness by rotary evaporation and the solids partitioned between 3:1 ethyl acetate/tetrahydrofuran and saturated potassium carbonate. The aqueous phase was extracted with 3:1 ethyl acetate/tetrahydrofuran (3×), the combined organics dried (Na$_2$SO$_4$), and concentrated to provide 2.11 g (100%) 6-(4-bromo-2-chlorophenylamino)-7-fluoro-3-methyl-3H-benzoimidazole-5-carboxylic acid (2-hydroxyethoxy)-amide as an off-white solid. MS ESI (+) m/z 457, 459 (M+, Br pattern) detected. $^1$H NMR (400 MHz, MeOH-d$_4$) δ 8.26 (s, 1H), 7.78 (s, 1H), 7.57 (d, 1H), 7.24 (dd, 1H), 6.40 (dd, 1H), 3.86 (s, 3H), 3.79 (m, 2H), 3.49 (m, 2H). $^{19}$F NMR (376 MHz, MeOH-d$_4$)-133.68 (s).

Example 2

Investigation of the Physical Properties of the Hydrogen Sulfate Salt

The product of Example 1 was subject to the following tests to determine its physical properties.

Powder X-Ray Diffraction (PXRD)

All samples were run on a Bruker D5000 diffractometer. The X-ray powder diffraction spectra were determined by mounting a sample of the crystalline salt on Siemens single silicon crystal (SSC) wafer mounts and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms. The collimated X-ray source was passed through an automatic variable divergence slit set at V20 and the reflected radiation directed through a 2 mm antiscatter slit and a 0.2 mm detector slit. The sample was exposed for 1 second per 0.02 degree 2-theta increment (continuous scan mode) over the range 2 degrees to 40 degrees 2-theta in theta-theta mode. The running time was 31 minutes and 41 seconds. The instrument was equipped with a scintillation counter as detector. Control and data capture was by means of a Dell Optiplex 686 NT 4.0 Workstation operating with Diffract+ software.

Data were collected over the range 2-theta 2-40°, in increments of 2-theta 0.02° with 4 s per increment and are categorized in Table 2, with relative intensities derived from diffractograms measured with fixed slits.

TABLE 2

| % Relative Intensity | Definition |
| --- | --- |
| 25-100 | VS—Very Strong |
| 10-25 | S—Strong |
| 3-10 | M—Medium |
| 1-3 | W—Weak |

The results of the scan are shown in FIG. 1, where the upper grey line represents the XRPD of the hydrogen sulfate salt of Compound 1 and the lower black line represent the free form. The most intense peaks, starting with most intense, are given in Table 3. The peak at 24.59° is particularly strong.

TABLE 3

| 2 theta scale | Relative intensity |
| --- | --- |
| 24.59 | VS |
| 20.97 | VS |
| 23.99 | S |
| 27.65 | S |
| 12.24 | S |
| 23.49 | S |
| 24.30 | S |
| 17.02 | S |
| 25.91 | S |
| 22.50 | M |

Persons skilled in the art of X-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values (see Jenkins, R. & Snyder, R. L., "Introduction to X-Ray Powder Diffractometry", John Wiley & Sons, 1996, for further information).

Example 3

In-Vivo Investigation

Study of Salts Versus Free Base in Dispersed Formulation

A study was performed in dogs to measure plasma levels of Compound 1 in fasted dogs following administration of 150 mg free base equivalent oral doses in 7.5 mL various dispersion formulations in pharmaceutically acceptable dispersing agents with Compound 1 contained as the free form or hydrogen sulfate salt.

Single doses of 150 mg were administered orally to fasted beagle dogs weighing 12-17 kg and about 2 to 6 years old on each of three dosing days. Each dosing day was 1 week apart.

All formulations were prepared extemporaneously just prior to dosing by adding 7.5 mL of the appropriate dispersing solution via a 10 mL disposable syringe, to vials containing 150 mg free base equivalents of the appropriate drug form, capping and vortex mixing for 30 seconds to form a dispersion.

The dispersion was removed from the vial using the disposable syringe and dosed to the animal via a gavage tube positioned into the stomach. The vials were rinsed twice by adding, for each of the two rinses, a separate 15 mL aliquot of water (total rinse volume=30 mL) via a 20 mL disposable syringe, capping, vortex mixing for 5 seconds, removing the wash solution from the vial using the disposable syringe and dosing to the animal via the gavage tube.

Dogs were fed about 400 g of Special Diet Services Laboratory Diet A each day and allowed water ad libitum. Whole blood (2 mL) in lithium heparin tubes were taken from the jugular vein immediately prior to dosing and at 0.5, 1, 2, 3, 4, 5, 6, 8, 12, 18, 24, 36 and 48 hours. The blood was centrifuged at 3000 rpm for 15 minutes and plasma was removed into plain blood tubes and the plasma stored at −20° C. until analysis.

Figure 3:
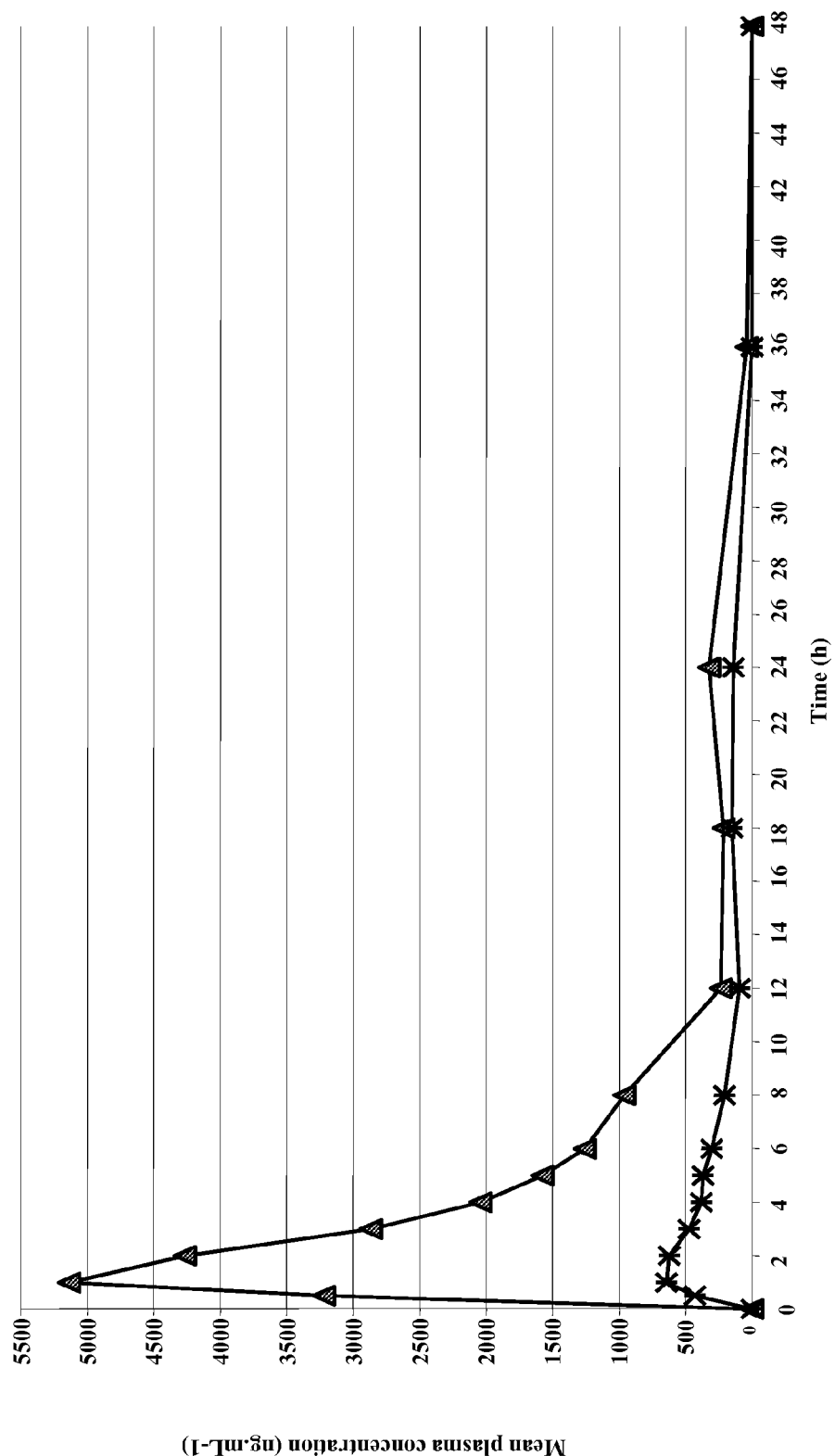
FIG. 3 shows the results of plasma concentration levels of Compound 1 following administration of 150 mg free base equivalent oral dispersion doses of Compound 1 (x) and the hydrogen sulfate salt to fasted dogs (▲).

Plasma (50 mcL) was analyzed for Compound 1 concentration. Two dogs were excluded from the analysis as they had vomited just after dosing. Mean plasma concentration profiles for Compound 1 seen after oral dosing are shown in FIG. 3 where the line represented by ▲ illustrates a formulation which included the hydrogen sulfate salt of Compound 1, and the line represented by x shows the results of Compound 1 free base in the same formulation.

It appears that formulation changes had a relatively small affect on exposure (results not shown). However when Compound 1 was dosed as the hydrogen sulfate salt, a substantial approximately 4 to 8 fold increase in exposure was produced.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A crystalline hydrogen sulfate salt of 6-(4-bromo-2-chloro-phenylamino)-7-fluoro-3-methyl-3H-benzoimidazole-5-carboxylic acid (2-hydroxy-ethoxy)-amide, wherein said hydrogen sulfate salt of 6-(4-bromo-2-chloro-phenylamino)-7-fluoro-3-methyl-3H-benzoimidazole-5-carboxylic acid (2-hydroxy-ethoxy)-amide has an X-ray powder diffraction pattern with specific peaks at about 2-theta equal to 24.59°, 20.97°, 27.65°, 12.24°, and 17.02°.

2. The crystalline hydrogen sulfate salt of 6-(4-bromo-2-chloro-phenylamino)-7-fluoro-3-methyl-3H-benzoimidazole-5-carboxylic acid (2-hydroxy-ethoxy)-amide according to claim 1, wherein said hydrogen sulfate salt of 6-(4-bromo-2-chloro-phenylamino)-7-fluoro-3-methyl-3H-benzoimidazole-5-carboxylic acid (2-hydroxy-ethoxy)-amide has an X-ray powder diffraction pattern with specific peaks at about 2-theta equal to 24.59°, 20.97°, 23.99°, 27.65°, 12.24°, 23.49°, 24.30°, 17.02°, 25.91° and 22.50°.

3. The crystalline hydrogen sulfate salt of 6-(4-bromo-2-chloro-phenylamino)-7-fluoro-3-methyl-3H-benzoimidazole-5-carboxylic acid (2-hydroxy-ethoxy)-amide according to claim 1, which has a powder X-ray diffraction pattern substantially the same as the X-ray powder diffraction pattern shown in FIG. 1.

4. The crystalline hydrogen sulfate salt of 6-(4-bromo-2-chloro-phenylamino)-7-fluoro-3-methyl-3H-benzoimidazole-5-carboxylic acid (2-hydroxy-ethoxy)-amide according to claim 1, wherein said hydrogen sulfate salt of 6-(4-bromo-2-chloro-phenylamino)-7-fluoro-3-methyl-3H-benzoimidazole-5-carboxylic acid (2-hydroxy-ethoxy)-amide has an X-ray powder diffraction pattern with specific peaks at about 2-theta equal to 24.59°, 20.97°, 27.65°, 12.24°, 23.49°, 23.99°, 17.02° and 25.91°.

5. A pharmaceutical composition comprising a crystalline hydrogen sulfate salt of 6-(4-bromo-2-chloro-phenylamino)-7-fluoro-3-methyl-3H-benzoimidazole-5-carboxylic acid (2-hydroxy-ethoxy)-amide, wherein said hydrogen sulfate salt of 6-(4-bromo-2-chloro-phenylamino)-7-fluoro-3-methyl-3H-benzoimidazole-5-carboxylic acid (2-hydroxy-ethoxy)-amide has an X-ray powder diffraction pattern with specific peaks at about 2-theta equal to 24.59°, 20.97°, 27.65°, 12.24° and 17.02°, and a pharmaceutically acceptable excipient.

6. The pharmaceutical composition of claim 5, in a form for oral administration.

7. The pharmaceutical composition of claim 6, formulated as a tablet, lozenge, hard or soft capsule, emulsion, dispersible powder or granule, syrup, elixir, oily suspension or aqueous suspension.

8. The pharmaceutical composition of claim 7, formulated as a tablet or hard or soft capsule.

9. A pharmaceutical composition comprising a crystalline hydrogen sulfate salt of 6-(4-bromo-2-chloro-phenylamino)-7-fluoro-3-methyl-3H-benzoimidazole-5-carboxylic acid (2-hydroxy-ethoxy)-amide, wherein said hydrogen sulfate salt of 6-(4-bromo-2-chloro-phenylamino)-7-fluoro-3-methyl-3H-benzoimidazole-5-carboxylic acid (2-hydroxy-ethoxy)-amide has an X-ray powder diffraction pattern with specific peaks at about 2-theta equal to 24.59°, 20.97°, 23.99°, 27.65°, 12.24°, 23.49°, 24.30°, 17.02°, 25.91° and 22.50°, and a pharmaceutically acceptable excipient.

10. The pharmaceutical composition of claim 9, in a form for oral administration.

11. The pharmaceutical composition of claim 10, formulated as a tablet, lozenge, hard or soft capsule, emulsion, dispersible powder or granule, syrup, elixir, oily suspension or aqueous suspension.

12. The pharmaceutical composition of claim 11, formulated as a tablet or hard or soft capsule.

13. A pharmaceutical composition, comprising a crystalline hydrogen sulfate salt of 6-(4-bromo-2-chloro-phenylamino)-7-fluoro-3-methyl-3H-benzoimidazole-5-carboxylic acid (2-hydroxy-ethoxy)-amide which has a powder X-ray diffraction pattern substantially the same as the X-ray powder diffraction pattern shown in FIG. 1, and a pharmaceutically acceptable excipient.

14. The pharmaceutical composition of claim 13, in a form for oral administration.

15. The pharmaceutical composition of claim 14, formulated as a tablet, lozenge, hard or soft capsule, emulsion, dispersible powder or granule, syrup, elixir, oily suspension or aqueous suspension.

16. The pharmaceutical composition of claim 15, formulated as a tablet or hard or soft capsule.

17. A pharmaceutical composition comprising a crystalline hydrogen sulfate salt of 6-(4-bromo-2-chloro-phenylamino)-7-fluoro-3-methyl-3H-benzoimidazole-5-carboxylic acid (2-hydroxy-ethoxy)-amide, wherein said hydrogen sulfate salt of 6-(4-bromo-2-chloro-phenylamino)-7-fluoro-3-methyl-3H-benzoimidazole-5-carboxylic acid (2-hydroxy-ethoxy)-amide has an X-ray powder diffraction pattern with specific peaks at about 2-theta equal to 24.59°, 20.97°, 27.65°, 12.24°, 23.49°, 23.99°, 17.02° and 25.91°, and a pharmaceutically acceptable excipient.

18. The pharmaceutical composition of claim 17, in a form for oral administration.

19. The pharmaceutical composition of claim 18, formulated as a tablet, lozenge, hard or soft capsule, emulsion, dispersible powder or granule, syrup, elixir, oily suspension or aqueous suspension.

20. The pharmaceutical composition of claim 19, formulated as a tablet or hard or soft capsule.

* * * * *

UNITED STATES PATENT AND TRADEMARK OFFICE
CERTIFICATE OF CORRECTION

PATENT NO. : 9,156,795 B2  
APPLICATION NO. : 13/463499  
DATED : October 13, 2015  
INVENTOR(S) : DeMattei et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 559 days.

Signed and Sealed this  
Twenty-fourth Day of May, 2016

Michelle K. Lee  
*Director of the United States Patent and Trademark Office*